(12) United States Patent
Lee et al.

(10) Patent No.: US 8,426,600 B2
(45) Date of Patent: Apr. 23, 2013

(54) METHOD FOR PREPARING MONTELUKAST SODIUM SALTS

(75) Inventors: In Sang Lee, Daejeon (KR); Seok Ju Lee, Daejeon (KR); Jae Eun Kang, Daejeon (KR)

(73) Assignee: LG Life Sciences, Ltd., Seoul (KR)

( * ) Notice: Subject to any disclaimer, the term of this patent is extended or adjusted under 35 U.S.C. 154(b) by 123 days.

(21) Appl. No.: 13/062,353

(22) PCT Filed: Sep. 25, 2009

(86) PCT No.: PCT/KR2009/005472
§ 371 (c)(1),
(2), (4) Date: Mar. 4, 2011

(87) PCT Pub. No.: WO2010/036048
PCT Pub. Date: Apr. 1, 2010

(65) Prior Publication Data
US 2011/0166356 A1  Jul. 7, 2011

(30) Foreign Application Priority Data
Sep. 26, 2008 (KR) .................. 10-2008-0094731

(51) Int. Cl.
*C07D 215/38* (2006.01)
(52) U.S. Cl.
USPC ......................................... 546/174

(58) Field of Classification Search .................. 546/174
See application file for complete search history.

(56) References Cited

U.S. PATENT DOCUMENTS

| 5,614,632 | A  | * | 3/1997 | Bhupathy et al. | 546/180 |
| 7,427,600 | B2 | * | 9/2008 | Mickle et al. | 514/1.1 |
| 8,252,806 | B2 | * | 8/2012 | Eriksen et al. | 514/266.23 |
| 2007/0208178 | A1 | | 9/2007 | Bran | 546/180 |

FOREIGN PATENT DOCUMENTS

| EP | 0 480 717 | 4/1992 |
| WO | 2005-105751 A1 | 11/2005 |
| WO | 2006-064269 A1 | 6/2006 |
| WO | 2008-017669 A1 | 2/2008 |
| WO | 2008-072872 A1 | 6/2008 |

* cited by examiner

*Primary Examiner* — D M Seaman
(74) *Attorney, Agent, or Firm* — Ladas & Parry LLP (57) ABSTRACT

Disclosed is a method for preparing a montelukast sodium salt of Formula 1. The method includes coupling a methanesulfonyl compound of Formula 2 below with a compound of Formula 3 below in the presence of a bistrimethylsilylamide alkali metal salt, further adding an alkali metal base thereto and hydrolyzing the mixture by heating to prepare a compound of Formula 4 below, reacting the compound of Formula 4 with 4-tert-butylcyclohexylamine, followed by purification, to prepare an amine salt of Formula 5, and converting the amine salt of Formula 5 into a sodium salt.

15 Claims, 4 Drawing Sheets

METHOD FOR PREPARING MONTELUKAST SODIUM SALTS

CROSS-REFERENCE TO RELATED APPLICATIONS

This application is the U.S. National Stage of International Patent Application No. PCT/KR2009/005472 filed on Sep. 25, 2009, which claims priority to Korean Patent Application Number 10-2008-0094731 filed on Sep. 26, 2008, the disclosures of which are hereby incorporated by reference in their entirety.

TECHNICAL FIELD

The present invention relates to a method for preparing a montelukast sodium salt. More preferably, the present invention relates to a method for preparing a montelukast sodium salt, comprising coupling a methanesulfonyl compound of Formula 2 below with a compound of Formula 3 below in the presence of a bistrimethylsilylamide alkali metal salt, further adding an alkali metal base thereto and hydrolyzing the mixture by heating to prepare a compound of Formula 4 below, reacting the compound of Formula 4 with 4-tert-butylcyclohexylamine, followed by purification, to prepare an amine salt of Formula 5, and converting the amine salt of Formula 5 into a sodium salt.

BACKGROUND ART

A montelukast sodium salt is a substance which exhibits efficacy of Singulair (available from Korean MSD) generally used for the treatment of asthma as well as for the symptoms associated with allergic rhinitis, which is pharmaceutically known as a leukotriene receptor antagonist. Leukotrienes produced in vivo by metabolic action of arachidonic acid include LTB4, LTC4, LTD4 and LTE4. Of these, LTC4, LTD4 and LTE4 are cysteinyl leukotrienes (CysLTs), which are clinically essential in that they exhibit pharmaceutical effects such as contraction of airway muscles and smooth muscles and promotion of secretion of bronchial mucus.

Montelukast sodium salt is a white and off-white powder which has physical and chemical properties that it is well soluble in ethanol, methanol and water and is practically insoluble in acetonitrile.

A conventionally known method for preparing a montelukast sodium salt is disclosed in EP Patent No. 480,717. However, the method in accordance with the EP Patent requires processes for introducing and then removing a tetrahydropyranyl (THP) protecting group and purification by chromatography, thus being disadvantageously unsuitable for mass-production. In addition, the method disadvantageously requires investment in high-cost equipment, for example, to obtain amorphous final compounds by lyophilization.

Meanwhile, U.S. Pat. No. 5,614,632 discloses an improved method for preparing a montelukast sodium salt by directly reacting a methanesulfonyl compound (2) with 1-(lithium mercaptomethyl)cyclopropaneacetic acid lithium salt, without using the tetrahydropyranyl protecting group used in EP Patent No. 480,717, purifying in the form of a dicyclohexylamine salt by adding dicyclohexylamine to the reaction solution, and converting the salt into a montelukast sodium salt (1).

However, the method in accordance with the US patent should use n-butyl lithium as a base in the process of preparing the 1-(lithium mercaptomethyl)cyclopropaneacetic acid lithium salt and thus requires an improved process due to drawbacks that n-butyl lithium is dangerous upon handling and is an expensive reagent.

PCT International Patent Laid-open No. WO 2005/105751 discloses a method for preparing a montelukast sodium salt, comprising coupling methyl 1-(mercaptomethyl)cyclopropane acetate (3) used in step 10 shown in Example 146 of EP Patent 480,717 with a methanesulfonyl compound (2) in the presence of a solvent/cosolvent/base, performing hydrolysis, recrystallizing the resulting montelukast acid (4) in the presence of a variety of solvents to obtain highly pure montelukast acid (4), and converting the same into a montelukast sodium salt (1).

In addition, WO 2005/105751 claims that, in the coupling reaction, one is selected from tetrahydrofurane and dimethylcarbonate as a solvent, a highly polar solvent is selected from dimethylformamide, dimethylacetamide and N-methylpyrrolidone as a cosolvent, and one is selected from sodium hydroxide, lithium hydroxide, sodium hydride, sodium methoxide, potassium tert-butoxide, lithium diisopropylamine and quaternary ammonium salts, as a base.

However, WO 2005/105751 discloses that, since the coupling reaction requires use of a mixed solvent and the mixed solvent is different from the solvent used for hydrolysis, a process for removing the cosolvent through distillation under reduced pressure or extraction is further required prior to hydrolysis.

Further, in accordance with the method of WO 2005/105751, recrystallization is performed in the presence of a variety of solvents in order to obtain a highly pure montelukast acid (4) and the resulting recrystallization yield is varied in a range of 30 to 80%, depending on the solvent. In the case where desired purity is not obtained, recrystallization is repeated until montelukast acid (4) with a desired purity can be obtained. Disadvantageously, the method causes deterioration in overall yield.

DISCLOSURE

Technical Problem

Therefore, the present invention has been made to solve the above problems and other technical problems that have yet to be resolved.

As a result of a variety of extensive and intensive studies and experiments to solve the problems as described above, the inventors of the present invention have discovered that, in the case where bistrimethylsilylamide alkali metal salt and 4-tert-butylcyclohexylamine are used in the process of preparing a montelukast sodium salt, the process for preparing a montelukast sodium salt can be simplified, is suitable for mass-production and enables preparation of montelukast sodium salt with high yield and high purity. The present invention was completed based on this discovery.

Technical Solution

Accordingly, the present invention provides a method for preparing a montelukast sodium salt of Formula 1 below, comprising:

(1)

(i) coupling a methanesulfonyl compound of Formula 2 below with a compound of Formula 3 below in the presence of a bistrimethylsilylamide alkali metal salt, further adding an alkali metal base thereto, hydrolyzing the mixture by heating to prepare a compound of Formula 4 below;

(2)

(3)

(4)

(ii) reacting the compound of Formula 4 with 4-tert-butyl-cyclohexylamine, followed by purification, to prepare an amine salt of Formula 5; and (5)

(iii) converting the amine salt of Formula 5 into a sodium salt.

Specifically, as depicted in the following reaction scheme, the montelukast sodium salt of Formula 1 is prepared by sulfonating a compound of Formula A with a compound such as methanesulfonyl chloride and benzyl sulfonate to prepare a methanesulfonyl compound of Formula 2, and performing a series of processes such as coupling reaction, hydrolysis, amine salt formation and finally converting into a sodium salt.

The method for preparing montelukast sodium salt according to the present invention can simplify the coupling and hydrolysis reactions by using a bistrimethylsilylamide alkali metal salt and improve efficiency of purification by using 4-tert-butylcyclohexylamine, thus being suitable for mass-production and enabling preparation of montelukast sodium salt with high yield and high purity.

The coupling reaction of step (i) may be carried out in a solvent allowing the coupling reaction without affecting chemical properties of the compound of Formula 2 and the compound of Formula 3. Preferably, the solvent may be selected from the group consisting of tetrahydrofuran, 2-methyltetrahydrofuran, dimethylformamide, dimethylacetamide, N-methylpyrrolidone and toluene.

Preferably, the bistrimethylsilylamide alkali metal salt that can be used for step (i) is one or more selected from the group consisting of lithium bistrimethylsilylamide, sodium bistrimethylsilylamide and potassium bistrimethylsilylamide.

In a preferred embodiment, the hydrolysis reaction of step (i) may be continuously carried out in the same reactor without any treatment process after the coupling reaction.

In the reaction process of step (i), the coupling reaction is performed in the presence of a bistrimethylsilylamide alkali metal salt, as can be demonstrated from the test results shown in the following Examples, montelukast acid (compound of Formula 4) can be obtained in high yield without further performing any process, to remove the solvent used for the coupling reaction, such as distillation under reduced pressure or extraction, prior to the hydrolysis reaction.

Accordingly, step (i) may omit other treatment processes such as distillation under reduced pressure or extraction, thus maintaining the high yield of montelukast acid and simplifying the overall preparation process of the montelukast sodium salt.

Any alkali metal base may be used for step (i) without particular limitation so long as it removes the methyl group from the compound of Formula 3 in the hydrolysis process to prepare the compound of Formula 4. Preferably, the alkali metal base is one or more selected from the group consisting of sodium hydroxide, lithium hydroxide and potassium hydroxide.

In step (i), the amount of the compound of Formula 3 should be controlled in order to prepare the compound of Formula 4 in high yield by reaction of the compound of Formula 3 with the methanesulfonyl compound of Formula 2. The compound of Formula 3 is preferably used in an amount of 1.0 to 2.0 eq, more preferably, 1.1 to 1.5 eq, with respect to the methanesulfonyl compound of Formula 2.

Meanwhile, the coupling reaction of step (i) is preferably carried out at a relatively low temperature, so that the methanesulfonyl compound of Formula 2 can be readily bonded to the compound of Formula 3 and, for example, the coupling reaction may be carried out at −20° C. to 0° C. for 1 to 10 hours.

In addition, the hydrolysis reaction of step (i) should be carried out at a suitable temperature range to minimize methylstyrene impurity formation, for example, the hydrolysis reaction may be carried out at 40° C. to 60° C. for about 5 to about 20 hours.

In step (ii), 4-tert-butylcyclohexylamine may be used as a single or mixed isomer compound, and for example, 4-tert-butylcyclohexylamine may be a trans single isomer or a cis/trans isomer mixture.

The reaction conditions of step (ii) are not particularly limited so long as they allow reaction between chemical properties of the compound of Formula 4 and 4-tert-butylcyclohexylamine to prepare the compound of Formula 5, without affecting chemical properties of the compound of Formula 4 and 4-tert-butylcyclohexylamine. Preferably, the reaction of step (ii) may be carried out in one or more solvents selected from the group consisting of acetone, acetonitrile, ethyl acetate, tetrahydrofuran, methylene chloride, chloroform, toluene, xylene, hexane, cyclohexane and heptane.

In addition, the amount of 4-tert-butylcyclohexylamine used should be controlled in order to prepare the compound of Formula 5 in high yield by reaction of the 4-tert-butylcyclohexylamine with the compound of Formula 4. The 4-tert-butylcyclohexylamine is preferably used in an amount of 1.0 to 3.0 eq. with respect to the compound of Formula 4.

Meanwhile, the reaction of step (ii) is preferably carried out at 0° C. to 90° C. so that the compound of Formula 4 can be smoothly crystallized, solidified and converted into an amine salt of Formula 5.

The reaction conditions of step (iii) are not particularly limited so long as the amine salt compound of Formula 5 can be converted into the montelukast sodium salt of Formula 1. Preferably, the reaction of step (iii) is carried out in one or more solvents selected from acetone, acetonitrile, ethyl acetate, butyl acetate, methanol, ethanol, isopropanol, toluene, hexane, cyclohexane, heptane, diisopropylether, tetrahydrofuran and methylethylketone. More preferably, the reaction may be carried out in a mixed solvent of toluene and heptane.

Meanwhile, the amine salt compound of Formula 5 is layer-separated in the presence of an organic solvent, water and acetic acid, an aqueous layer is removed, the solvent of the organic layer is distilled under reduced pressure, methanol and sodium hydroxide are added to the residue, followed by stirring, to obtain a montelukast sodium salt solution and the solution is slowly added dropwise to a heptane solvent, to obtain the montelukast sodium salt solid.

The present invention also provides an amine salt compound of Formula 5 obtained as an intermediate in the process of preparing the montelukast sodium salt. The amine salt compound of Formula 5 is a novel compound. The amine salt compound of Formula 5 may be converted into a sodium salt using the organic solvent as mentioned above, methanol and sodium hydroxide, to prepare a montelukast sodium salt with a high yield and a high purity.

The X-ray diffraction spectrum of the amine salt is varied, depending on the solvent used, as shown in FIGS. 1 to 4.

As mentioned above, the 4-tert-butylcyclohexylamine used for the preparation process may be a trans single isomer or a cis/trans isomer mixture, but the amine salt compound of Formula 5 obtained therefrom may be a trans single isomer compound, as can be seen from the following Example 15.

BRIEF DESCRIPTION OF THE DRAWINGS

The above and other objects, features and other advantages of the present invention will be more clearly understood from the following detailed description taken in conjunction with the accompanying drawings, in which.

BEST MODE

Now, the present invention will be described in more detail with reference to the following Examples. These examples are provided only to illustrate the present invention and should not be construed as limiting the scope and spirit of the present invention.

EXAMPLE 1

Preparation of 2-(2-(3(S)-(3-(7-chloro-2-quinolinyl)-ethenyl)phenyl)-3 methanesulfonyloxypropyl)phenyl-2-propanol (2)

2-(2-(3(S)-(3-(7-chloro-2-quinolinyl)-ethenyl)phenyl)-3-hydroxypropyl)phenyl-2-propanol (20.0 g) was dissolved in 70 ml of tetrahydrofuran, the reactor temperature was decreased to 0° C. and diisopropylethylamine (8.43 ml) was slowly added dropwise thereto. The inner temperature of the reactor was reduced to −25° C., methanesulfonyl chloride (5.54 g) was slowly added dropwise under nitrogen, and the reaction mixture was stirred at −25° C. for one hour. After completion of the reaction, 200 ml of acetonitrile was slowly added dropwise at an inner reactor temperature of −20° C. or lower. The resulting solid was filtered under nitrogen using a low-temperature filter, washed with 100 ml of acetonitrile cooled to 0° C. or lower and dried to obtain 21.7 g of the title compound as a pale yellow solid.

$^1$H NMR (400 MHz, CDCl$_3$): δ 8.12(m, 2H), 7.75(m, 3H), 7.66(d, 2H), 7.42(m, 5H), 7.19(m, 3H), 5.73(dd, 1H), 3.27(m, 1H), 3.07(m, 1H), 2.80(s, 3H), 2.50(m, 1H), 2.30(m, 1H), 1.68(s, 6H).

EXAMPLE 2

Preparation of [R-(E)]-1-[[[3-[2-(7-chloro-2-quinolinyl)ethenyl]phenyl]-3-[2-(1-hydroxy-1-methylethyl)phenyl]propyl]thio]methyl]cyclopropaneacetic acid (4)

1-(mercaptomethyl)cyclopropaneacetic acid methyl ester (1.37 g) was dissolved in 15 ml of tetrahydrofuran and the inner reactor temperature was cooled to −15° C. Sodium bistrimethylsilylamide (2M tetrahydrofuran solution, 4.8 ml) was added dropwise to the reaction mixture under nitrogen, followed by stirring at −15° C. for one hour. The compound (4.0 g) prepared in Example 1 was added thereto at this reaction temperature, followed by stirring for 7 hours. After completion of the coupling reaction, the inner reactor temperature was elevated to room temperature and a 10% aqueous lithium hydroxide solution (12 g) was added thereto. The inner reactor temperature was elevated to 50° C. and reacted at this temperature for 10 hours. After completion of the reaction, the reaction solution was cooled to room temperature, 30 ml of acetic acid was slowly added to adjust the pH to 5, 50 ml of ethyl acetate and 30 ml of a 10% sodium chloride aqueous solution were added thereto, an organic layer was separated, and the organic layer was washed with 20 ml of water, dried over sodium sulfate and distilled under reduced pressure to remove the solvent to obtain 4.17 g of the title compound (purity 92.4%) as a yellow solid.

EXAMPLES 3 to 8

The reaction was carried out in the same manner as in Example 2, except that the types of solvent and base were varied. The results thus obtained are shown in Table 1 below.

TABLE 1

| | Solvent | Base | Yield % |
|---|---|---|---|
| Ex. 3 | Tetrahydrofuran | Sodium bistrimethylsilylamide (95%) | 84.7 |
| Ex. 4 | Tetrahydrofuran | Lithium bistrimethylsilylamide (95%) | 68.7 |
| Ex. 5 | Tetrahydrofuran | Potassium bistrimethylsilylamide (95%) | 84.5 |
| Ex. 6 | Dimethylformamide | Sodium bistrimethylsilylamide (95%) | 82.1 |
| Ex. 7 | Dimethylformamide | Lithium bistrimethylsilylamide (95%) | 83.5 |
| Ex. 8 | 3-methyltetrahydrofuran | Potassium bistrimethylsilylamide (95%) | 66.4 |

*95%: purity of reactant

As can be seen from Table 1 above, in accordance with the method of the present invention, the compound of Example 2 (compound of Formula 4) prepared by coupling the methanesulfonyl compound (compound of Formula 2) with a 1-(mercaptomethyl)cyclopropaneacetic acidmethyl ester compound (compound of Formula 3) using a bistrimethylsilylamide alkali metal salt and continuously performing hydrolysis in the same reactor without any additional treatment process exhibited the overall high yield, and, in particular, the compound (the title compound of Example 2) prepared as a bistrimethylsilylamide alkali metal salt using sodium bistrimethylsilylamide (Example 3) or potassium bistrimethylsilylamide (Example 5) exhibited a relatively high yield.

EXAMPLE 9

Preparation of [R-(E)]-1-[[[3-[2-(7-chloro-2-quinolinyl)ethenyl]phenyl]-3-[2-(1-hydroxy-1-methylethyl)phenyl]propyl]thio]methyl]cyclopropaneacetic acid 4-tert-butylcyclohexylamine salt (5)

The compound prepared in Example 2 (4.17 g, purity 92.4%) was dissolved in 60 ml of ethyl acetate and 2.0 g of 4-tert-butylcyclohexylamine (cis:trans=1:1 mixture) was added thereto at room temperature. The reaction temperature was elevated to 80° C., and the reaction mixture was stirred for one hour and was slowly cooled to room temperature. At this time, the reaction solution was crystallized and solidified. Upon completion of solidification, the reaction solution was slowly stirred, while 80 ml of hexane was slowly added dropwise. The reaction solution was stirred at room temperature for about 3 hours, filtered using a filter, washed with hexane and dried to obtain 4.3 g of the title compound as an off-white solid (purity 98.7% and optically active purity 99.8% e.e.)

$^1$H NMR (400 MHz, CDCl$_3$): δ 8.12(d, 1H), 8.09(d. 1H), 7.70(m, 4H), 7.30~7.51(m, 6H), 7.15(m, 3H), 4.02(t, 1H), 3.23(m, 1H), 2.85(m, 2H), 2.61(s, 2H), 2.37(s, 2H), 2.19~2.33(m, 2H), 2.05(d, 2H), 1.78(d, 2H), 1.63(d, 6H). 1.29(m, 2H), 0.98(m, 3H), 0.82(s, 9H), 0.34~0.57(m, 4H)

Figure 1:
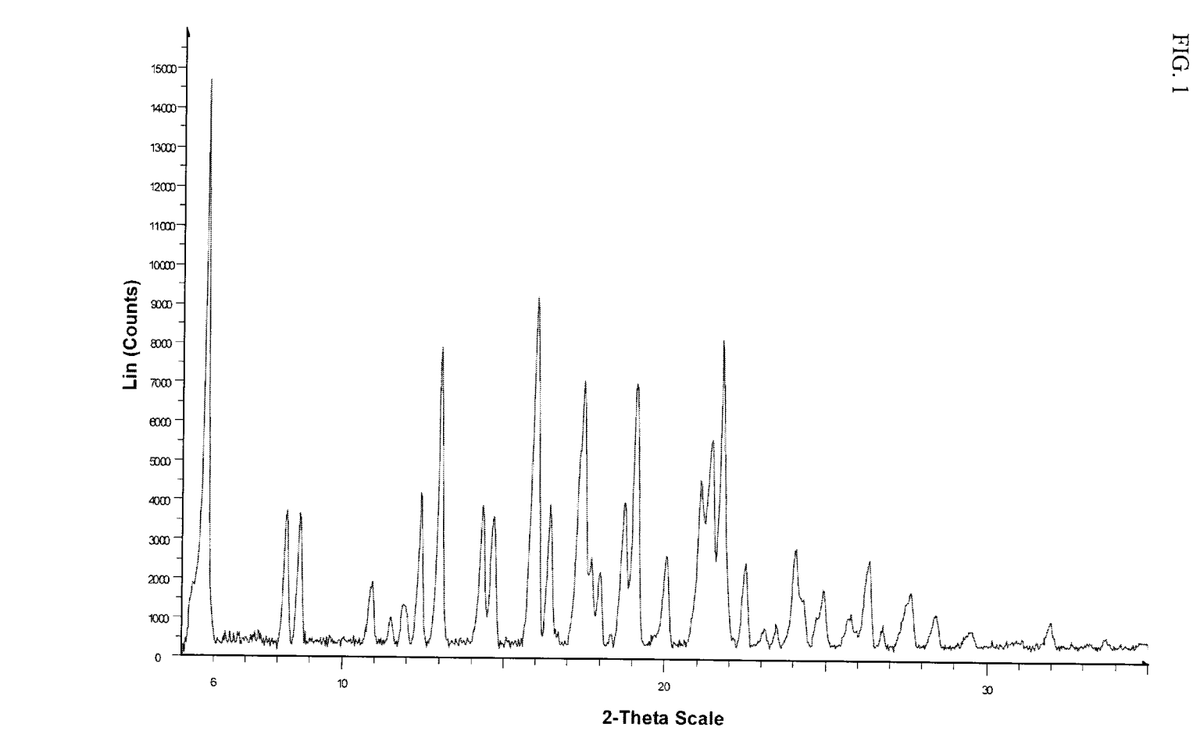
FIG. 1 is a graph showing the X-ray diffraction spectrum of the amine salt compound of Formula 5 obtained in Example 9 according to the present invention.
Figure 2:
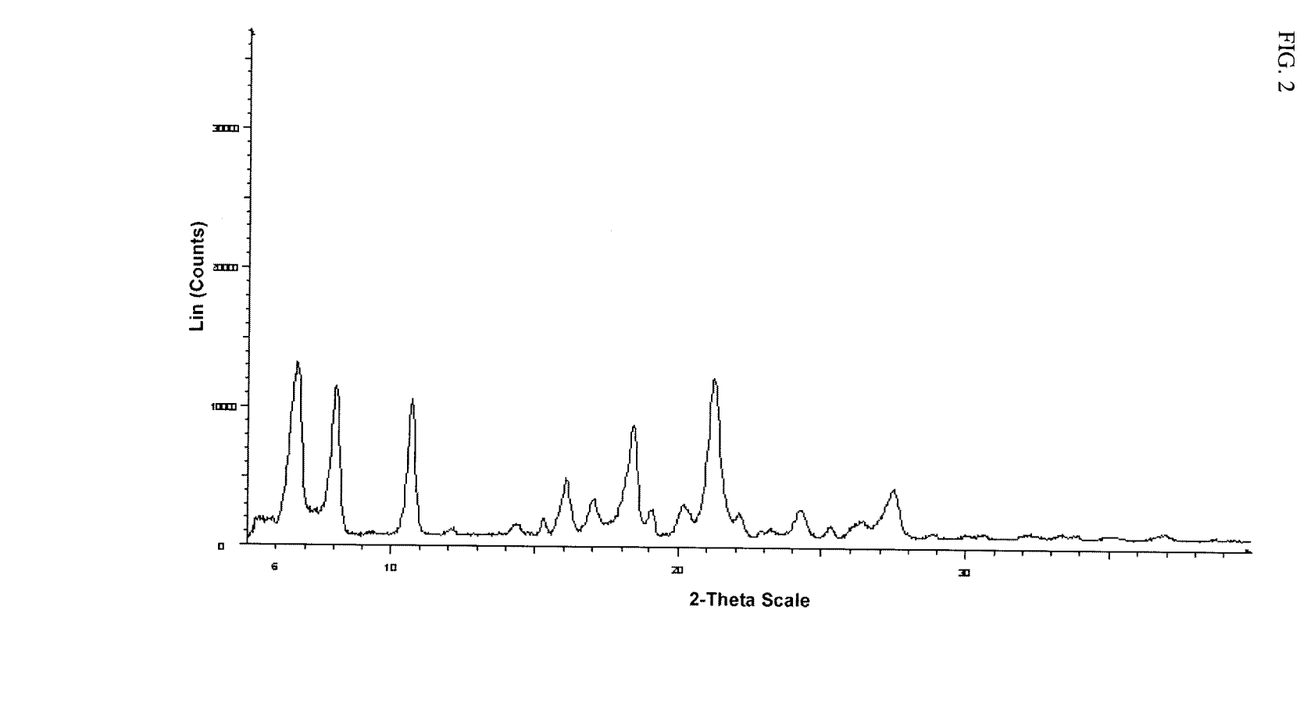
FIG. 2 is a graph showing the X-ray diffraction spectrum of the amine salt compound of Formula 5 obtained in Example 10 according to the present invention.

The X-ray diffraction spectrum of compound of Example 9 thus prepared (amine salt compound of Formula 5) is shown in FIG. 1.

EXAMPLE 10

Preparation of [R-(E)]-1-[[[3-[2-(7-chloro-2-quinolinyl)ethenyl]phenyl]-3-[2-(1-hydroxy-1-methylethyl)phenyl]propyl]thio]methyl]cyclopropaneacetic acid 4-tert-butylcyclohexylamine salt (5)

The compound prepared in Example 2 (4.17 g, purity 92.4%) was dissolved in 60 ml of toluene and 2.0 g of 4-tert-butylcyclohexylamine (cis:trans=1:1 mixture) was added thereto at room temperature. The reaction temperature was elevated to 80° C. and the reaction mixture was stirred for one hour and was slowly cooled to room temperature. At this time, the reaction solution was crystallized and solidified. Upon completion of crystallization, the reaction solution was slowly stirred, while 80 ml of hexane was slowly added dropwise thereto. The reaction solution was stirred at room temperature for about 3 hours, filtered using a filter, washed with hexane, and dried to obtain 4.8 g of the title compound as an off-white solid (purity 98.9% and optically active purity 99.8% e.e.).

Figure 3:
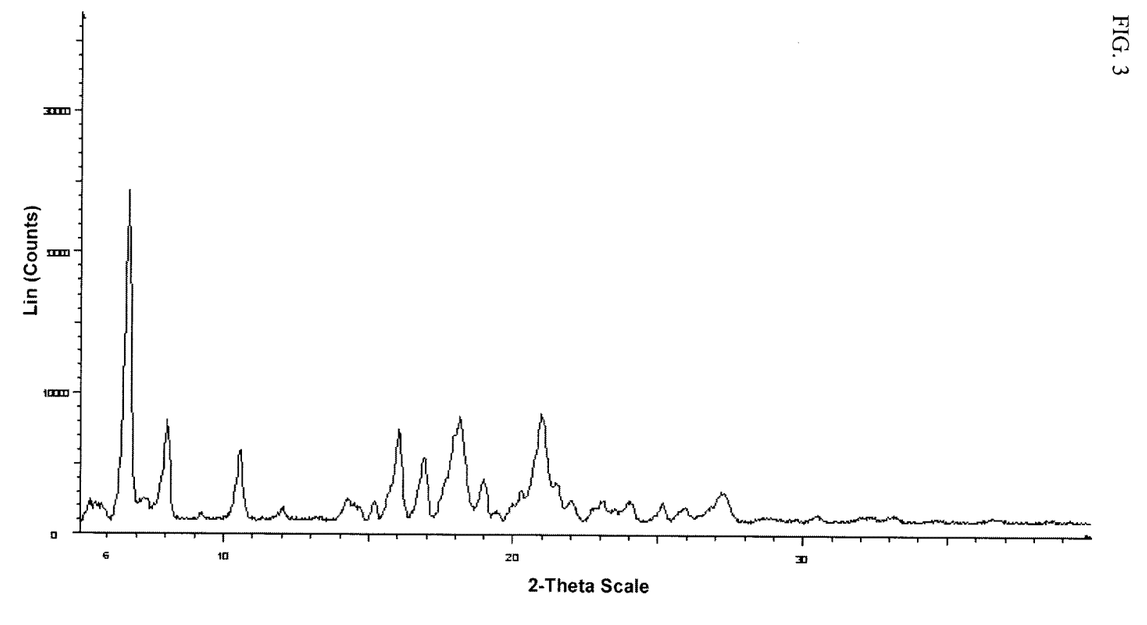
FIG. 3 is a graph showing the X-ray diffraction spectrum of the amine salt compound of Formula 5 obtained in Example 11 according to the present invention.

The X-ray diffraction spectrum of the compound of Example 10 thus prepared (amine salt compound of Formula 5) is shown in FIG. 3.

EXAMPLE 11

Preparation of [R-(E)]-1-[[[3-[2-(7-chloro-2-quinolinyl)ethenyl]phenyl]-3-[2-(1-hydroxy-1-methylethyl)phenyl]propyl]thio]methyl]cyclopropaneacetic acid 4-tert-butylcyclohexylamine salt (5)

The compound prepared in Example 2 (4.17 g, purity 92.4%) was dissolved in 60 ml of toluene and 2.0 g of 4-tert-butylcyclohexylamine (cis:trans=1:1 mixture) was added thereto at room temperature. The reaction temperature was elevated to 80° C. and the reaction mixture was stirred for one hour and slowly cooled to room temperature. At this time, the reaction solution was crystallized and solidified. Upon completion of crystallization, the reaction solution was slowly stirred, while 80 ml of acetonitrile was slowly added dropwise. The reaction solution was stirred at room temperature for about 3 hours, filtered using a filter, washed with acetonitrile and dried to obtain 4.4 g of the title compound as an off-white solid (purity 98.8% and optically active purity 99.8% e.e.)

The X-ray diffraction spectrum of compound of Example 11 thus prepared (amine salt compound of Formula 5) is shown in FIG. 3.

EXAMPLE 12

Preparation of [R-(E)]-1-[[[3-[2-(7-chloro-2-quinolinyl)ethenyl]phenyl]-3-[2-(1-hydroxy-1-methylethyl)phenyl]propyl]thio]methyl]cyclopropaneacetic acid 4-tert-butylcyclohexylamine salt (5)

The compound prepared in Example 2 (4.17 g, purity 92.4%) was dissolved in 60 ml of toluene and 2.0 g of 4-tert-butylcyclohexylamine (cis:trans=1:1 mixture) was added thereto at room temperature. The reaction temperature was elevated to 80° C. and the reaction mixture was stirred for one hour and was slowly cooled to room temperature. At this time, the reaction solution was crystallized and solidified. Upon completion of crystallization, the reaction solution was slowly stirred, while 80 ml of heptane was slowly added dropwise. The reaction solution was stirred at room temperature for about 3 hours, filtered using a filter, washed with heptane and dried to obtain 4.7 g of the title compound as an off-white solid (purity 98.9% and optically active purity 99.8% e.e.)

Figure 4:
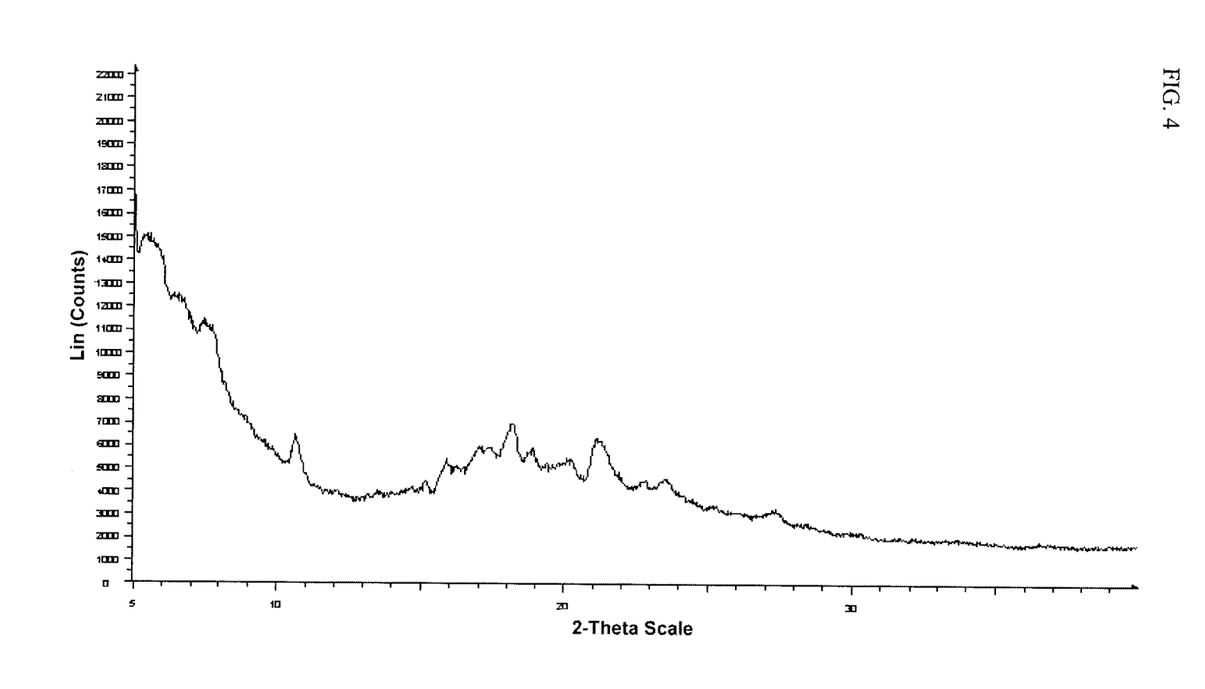
FIG. 4 is a graph showing the X-ray diffraction spectrum of the amine salt compound of Formula 5 obtained in Example 12 according to the present invention.

The X-ray diffraction spectrum of the compound of Example 12 thus prepared (amine salt compound of Formula 5) is shown in FIG. 4.

EXAMPLE 13

Preparation of [R-(E)]-1-[[[3-[2-(7-chloro-2-quinolinyl)ethenyl]phenyl]-3-[2-(1-hydroxy-1-methylethyl)phenyl]propyl]thio]methyl]cyclopropaneacetic acid sodium salt (1)

20 ml of toluene and 20 ml of water were added dropwise to the compound (4.3 g) prepared in Example 9, acetic acid was slowly added thereto to adjust the pH to 4 to 5, and stirred at room temperature for about 20 minutes. After the reaction mixture was separated into an organic layer and an aqueous layer, the resulting organic layer was washed with 20 ml of water. The organic layer thus obtained was concentrated, 40 ml of toluene was added dropwise thereto, a 10% sodium hydroxide methanol solution was slowly added dropwise at room temperature, followed by stirring for about 30 minutes. The resulting reaction mixture was concentrated, 40 ml of toluene was added thereto and the solution was slowly added dropwise to 80 ml of heptane contained in a separate reactor. At this time, the reaction solution was crystallized and solidified. Upon completion of crystallization, the reaction solution was slowly stirred at room temperature for one hour. The reaction solution was filtered using a filter, washed with heptane and dried to obtain 3.35 g of the title compound as an off-white solid (purity 99.7% and optically active purity 99.8% e.e.).

$^1$H NMR (400 MHz, CD3OD): δ 8.31(d, 1H), 8.01(s. 1H), 7.89(t, 2H), 7.81(d, 1H), 7.73(s, 1H), 7.58(d, 1H), 7.52(d, 1H), 7.46~7.41(m, 4H), 7.16~7.07(m, 3H), 4.06(s, 1H), 3.10

(m, 1H), 2.85(m, 1H), 2.67(d, 1H), 2.52(d, 1H), 2.40(d, 1H), 2.32(d, 1H), 2.25~2.17(m, 2H), 1.53(d, 6H). 0.59~0.33(m, 4H)

EXAMPLE 14

Confirmation of trans isomer structure of [R-(E)]-1-[[[3-[2-(7-chloro-2-quinolinyl)ethenyl]phenyl]-3-[2-(1-hydroxy-1-methylethyl)phenyl]propyl]thio]methyl]cyclopropaneacetic acid 4-tert-butylcyclohexylamine salt (5)

40 ml of ethyl acetate and 30 ml of water were added dropwise to the compound (1.0 g, purity>99%) prepared in Example 9, 7.5% tartaric acid was slowly added thereto to adjust the pH to 4 to 5, followed by stirring at room temperature for about 30 minutes. After the reaction mixture was separated into an organic layer and an aqueous layer, the resulting aqueous layer was completely concentrated under reduced pressure to obtain a crystalline 4-tert-butylcyclohexylamine tartaric acid salt (0.39 g). The 4-tert-butylcyclohexylamine tartaric acid salt was completely dissolved in 15 ml of water, 4N sodium hydroxide was slowly added dropwise and the resulting solid was filtered and dried under nitrogen to obtain a white solid.

The $^{13}$C-NMR analysis values of the 4-tert-butylcyclohexylamine thus obtained and 4-tert-butylcyclohexylamine tartaric acid salt previously obtained were compared with chemical shifts reported in the reference [H. J. Schneider and V. Hoppen, J. Org. Chem., 43, 3866 (1978)]. The results thus obtained are shown in Table 2 below. It can be confirmed that the amine salt compound of Formula 5 is a trans isomer.

TABLE 2

| | Carbon Number | | | | | |
|---|---|---|---|---|---|---|
| | 1 | 2 | 3 | 4 | 5 | 6 |
| Reference (trans) | 50.82 | 37.37 | 26.26 | 47.38 | 32.23 | 27.67 |
| 4-tert-butylcyclohexylamine | 50.77 | 35.76 | 26.06 | 47.19 | 32.31 | 27.59 |
| 4-tert-butylcyclohexylamine tartrate | 49.67 | 32.02 | 25.15 | 46.46 | 31.84 | 27.39 |
| Reference (cis) | 44.98 | 33.92 | 20.66 | 48.36 | 32.43 | 27.67 |

INDUSTRIAL APPLICABILITY

As apparent from the fore-going, advantageously, the method for preparing a montelukast sodium salt can simplify the coupling and hydrolysis reactions and improve efficiency of purification, thus being suitable for mass-production and enabling preparation of montelukast sodium salt with high yield and high purity.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for preparing a montelukast sodium salt of Formula 1 below, comprising:

(i) coupling a methanesulfonyl compound of Formula 2 below with a compound of Formula 3 below in the presence of a bistrimethylsilylamide alkali metal salt, further adding an alkali metal base thereto, and hydrolyzing the mixture by heating to prepare a compound of Formula 4 below;

(ii) reacting the compound of Formula 4 with 4-tert-butyl-cyclohexylamine, followed by purification to prepare an amine salt of Formula 5; and (iii) converting the amine salt of Formula 5 into a sodium salt.

2. The method according to claim 1, wherein the coupling reaction of step (i) is carried out in a single solvent selected from the group consisting of tetrahydrofuran, 2-methyltetrahydrofuran, dimethylformamide, dimethylacetamide, N-methylpyrrolidone and toluene.

3. The method according to claim 1, wherein the bistrimethylsilylamide alkali metal salt of step (i) is one or more selected from the group consisting of lithium bistrimethylsilylamide, sodium bistrimethylsilylamide and potassium bistrimethylsilylamide.

4. The method according to claim 1, wherein the hydrolysis reaction of step (i) is continuously carried out in the same reactor without any treatment process after the coupling reaction.

5. The method according to claim 1, wherein the alkali metal base of step (i) is one or more selected from the group consisting of sodium hydroxide, lithium hydroxide and potassium hydroxide.

6. The method according to claim 1, wherein, in step (i), the compound of Formula 3 is used in an amount of 1.0 to 2.0 eq with respect to the methanesulfonyl compound of Formula 2.

7. The method according to claim 1, wherein the coupling reaction of step (i) is carried out at −20° C. to 0° C.

8. The method according to claim 1, wherein the hydrolysis reaction of step (i) is carried out at a temperature of 40° C. to 60° C.

9. The method according to claim 1, wherein the 4-tert-butylcyclohexylamine of step (ii) is a trans single isomer or a cis/trans isomer mixture.

10. The method according to claim 1, wherein the reaction of step (ii) is carried out in one or more solvents selected from the group consisting of acetone, acetonitrile, ethyl acetate, tetrahydrofuran, methylene chloride, chloroform, toluene, xylene, hexane, cyclohexane and heptane.

11. The method according to claim 1, wherein the 4-tert-butylcyclohexylamine of step (ii) is used in an amount of 1.0 to 3.0 eq with respect to the compound of Formula 4.

12. The method according to claim 1, wherein the reaction of step (ii) is preferably carried out at a temperature of 0° C. to 90° C.

13. The method according to claim 1, wherein the reaction of step (iii) is carried out in one or more solvents selected from acetone, acetonitrile, ethyl acetate, butyl acetate, methanol, ethanol, isopropanol, toluene, hexane, cyclohexane, heptane, diisopropylether, tetrahydrofuran and methylethylketone.

14. An amine salt compound of Formula 5 below.

15. The compound according to claim 14, wherein the amine salt compound is a single trans isomer.

* * * * *